(12) United States Patent
Peng

(10) Patent No.: US 7,217,848 B2
(45) Date of Patent: May 15, 2007

(54) TRIDENTATE PHOSPHINES AND METHOD OF FORMING ALDEHYDE HYDROGENATION CATALYSTS

(75) Inventor: Wei-Jun Peng, Hurricane, WV (US)

(73) Assignee: Dow Global Technologies Inc., Midland, MI (US)

( * ) Notice: Subject to any disclaimer, the term of this patent is extended or adjusted under 35 U.S.C. 154(b) by 211 days.

(21) Appl. No.: 10/998,533

(22) Filed: Nov. 29, 2004

(65) Prior Publication Data

US 2006/0116536 A1 Jun. 1, 2006

(51) Int. Cl.
C07C 29/14 (2006.01)
C07C 27/00 (2006.01)
C07C 27/26 (2006.01)
C07C 45/00 (2006.01)

(52) U.S. Cl. ............... 568/880; 568/878; 568/914; 568/451; 568/454

(58) Field of Classification Search ............... 568/878, 568/880, 914, 451, 454
See application file for complete search history.

(56) References Cited

U.S. PATENT DOCUMENTS

| | | | |
|---|---|---|---|
| 3,590,087 | A | 6/1971 | Van Winkle |
| 3,663,622 | A | 5/1972 | Van Winkle |
| 4,687,866 | A | 8/1987 | Oswald et al. |
| 5,300,898 | A | 4/1994 | Chen et al. |
| 6,426,437 | B1 | 7/2002 | Shum |

FOREIGN PATENT DOCUMENTS

| | | |
|---|---|---|
| CN | 1275439 | 12/2000 |
| DE | 1909619 | 2/1968 |
| EP | 420510 | 9/1990 |
| GB | 2306344 | 10/1995 |
| WO | WO 9739995 | 10/1997 |
| WO | WO 2001070660 | 9/2001 |
| WO | WO 2004026800 | 4/2004 |
| WO | WO 2004054946 | 7/2004 |

OTHER PUBLICATIONS

Walter Strohmeier and Luise Weigelt, Journal of Organometallic Chemistry, 145 (1978) 189-194.
Nick Bampos et al., J. Inorg. Chem. 1993, 32, 4084-4088.
Hiroshi Fujitsu et al., J. Org. Chem. 1981, 46, 5353-5357.
R. A. Sanchez-Delgado et al., J. of Organometellic Chemistry, 209 (1981) 77-83.
Lisa M. Green and Devon W. Meek, Polyhedron 1990, vol. 9, No. 1, 35-45.
Frank Sussmilch, Wolfgang Glockner and dieter Rehder, J. of Organometallic Chemistry, 388 (1990) 95-104.
Abstract CN 1275439 A UPAB: 20010421.
Cotton, F. Albert, et al., "Polydentate Phosphines: Their Synthesis, Structural Aspects, and Selected Applications", Progress in Inorganic Chemistry, 1992, pp. 179-289, vol. 40.
Dahlenburg, L. et al., *Chemische Berichte*, vol. 121, No. 12, pp. 2083-2093 (1988).
Dubois, D. L. et al., "Rapid Homogenation of Olefins by Hydrido-Cobalt and -Rhodium Complexes of Chelating Trisphosphines," Inorganica Chimica Actai, vol. 19, pp. L29-L30 (1976).
European Patent Office: Patent Abstracts of Japan, Japanese Patent 62145033, Mitsubishi Chem Ind Ltd, "Production of Alcohol", Jul. 26, 1987.
Goikhman, Roman, et al., "New Tridentate Phosphine Rhodium and Iridium Complexes, Including a Stable Rhodium(I) Silyl. Si-S Activation and a Strong Effect of X in $(PP_2)M$-X (X= H, CI, Me) on Si-H Activation", Organometallics, 2002, pp. 5060-5065, vol. 21, No. 23.
Johnson, Carl R., et al., "Synthesis of Polydentate Ligands with Homochiral Phosphine Centers", J. Org. Chem. 1987, pp. 2170-2174, vol. 52, No. 11.
Lee, Hon Man, et al., Preparation and catalytic hydrogenation properties of some rhodium and ruthenium complexes with chiral tridentate phosphine ligands (s,S)-$PhP(CH_2CHMeCH_2 PPH_2)_2$ and (S)-$Ph_2PCH_2CH(PPh_2)CH_2 CH_2 PPh_2$), Journal of Organometallic Chemistry, 2000, pp. 330-334, 601.
Niewahner, James, et al., "In Situ Generation of the Hydrogenation Catalysts RhH(ttp) and RhH(Cyttp), ttp = $PhP(CH_2CH_2CH_2-PPh_2)_2$ and Cyttp = $Php(CH_2 CH_2 CH_2PCy_2)_2$, by Treating the RhCI(triphosphine) Complexes with either $AIEt_3$ or $AIEt_2Cl$", Inorganica Chimica Acta, 1982, pp. L123-L125, 64.

*Primary Examiner*—J. Parsa

(57) ABSTRACT

This invention comprises a process for hydrogenation of aldehydes to alcohols using novel homogeneous catalysts. The catalysts are generated in situ under hydrogen and carbon monoxide gases in a suitable solvent, by mixing a rhodium catalyst precursor, such as $Rh(CO)_2$ acetoacetonate and a defined ligand.

9 Claims, 1 Drawing Sheet

US 7,217,848 B2

TRIDENTATE PHOSPHINES AND METHOD OF FORMING ALDEHYDE HYDROGENATION CATALYSTS

BACKGROUND OF THE INVENTION

1. Field of the Invention

The invention relates to processes for hydrogenation of aldehydes to alcohols using certain novel rhodium complexes as homogeneous catalysts.

2. Description of the Prior Art

Hydrogenation of aldehydes to alcohols is an important part of oxo alcohol process. Most oxo alcohol processes use heterogeneous catalysts to accomplish the hydrogenation of aldehydes to alcohols although the aldehydes are produced using homogeneous catalysts. Continuing efforts have been devoted towards improving both the catalysts and processes of the hydrogenation reaction. For example, a) WO2004026800 A1, 20040401, "Process for production of an alcohol by the catalytic hydrogenation of a hydroformylation reaction-produced aldehyde in the presence of an organic sulfur compound" (Brown, Alistair Chalmers Ramsay. Johnson Matthey PLC, UK), described A process for the production of an alcohol (e.g., 3,5,5-trimethylhexanol) by hydrogenation of an aldehyde (e.g., 3,5,5-trimethylhexanal) over a copper and zinc-containing catalyst comprises the step of treating the reduced catalyst with a sulfur compound (e.g., thiophene). The process reduces the hydrogenation of olefin contained in the aldehyde feed compared with a process using an untreated catalyst; and b) CN1275439 A, 20001206, "Preparation and application of liquid-phase hydrogenation catalyst", (Wang, Xiuling; Li, Dongli; Zhu, Xubo. Beijing Institute of Chemical Engineering, China Petro-Chemical Co., Ltd., Peop. Rep. China), described a new catalyst that contains Ni 5–40, Co 0.2–5.0, Mo 0.2–5.0, Cr 0.5–6, K 0.5–2%, and carrier. The catalyst is prepared by mixing $SiO_2$ or diatomite, water, and binder, forming by extrusion, drying, calcining to obtain carrier, impregnating the carrier in a solution containing the salt of Ni, Co, Cr, K, and Mo, and drying. The catalyst is used in hydrogenation of aldehyde to prepare saturated alcohols.

Although unmodified cobalt catalyst and trialkylphosphine modified cobalt and rhodium catalysts have been used to produce alcohols directly from olefins, only a few oxo alcohol producers operate such "one-step" processes to produce alcohols from olefins. The limited utility of these catalysts is due to low regio- and chemo-selectivity, e.g. high degree of isomerization of alpha-olefins to internal olefins and low linear to branched product selectivity. An earlier patent from Shell, c) DE 1909619, for example, described the use of a phosphine modified cobalt catalyst to convert 1-dodecene (98.5 wt % conversion) to yield unsaturated hydrocarbons (14%), n-tridecanol (50.9%), and branched primary alcohols (33.4%).

There are continued efforts in improving such "one-step" processes. For example: d) WO2004054946 A1, 2004 Jul. 1, "Hydroformylation process for the conversion of an ethylenically unsaturated compound to an alcohol" (Drent, Eit; Suykerbuyk, Jacoba Catherina Lucia Johanna, Shell Internationale Research Maatschappij B.V., Neth.), described a hydroformylation process for the conversion of an ethylenically unsaturated compound to an alcohol comprising a first step of reacting at an elevated temperature in a reactor the ethylenically unsaturated compound, carbon monoxide, hydrogen, and a phosphine-containing cobalt hydroformylation catalyst, which are dissolved in a solvent, followed by a second step of separating a mixture comprising the alcohol and heavy ends from a solution comprising the catalyst and the solvent, followed by a third step of recycling the solution to the reactor; and e) EP 420510 A2, 1991 Apr. 3, "Process for the preparation of alcohols" (Cole-Hamilton, David J.; Macdougall, Joanna K.; Green, Michael James. British Petroleum Co. PLC, UK), described a process comprising reacting an olefin $R_2CH:CHR_1$ [$R_1$, $R_2$=H, (substituted) $C_{1-10}$ alkyl, —$C_{6-12}$ aryl, $C_{1-10}$ alkenyl] with CO and optionally H in presence of $C_{1-20}$ aliphatic alcohol solvent and a catalyst comprising $PR_3$ (R=$C_{1-10}$ alkyl) and a Rh component, to give an alcohol that has 1 C more than the reactant olefin; f) WO 9739995 A1, 1997 Oct. 30, "Preparation of unsaturated alcohols" (Guram, Anil Sakharam; Briggs, John Robert; Olson, Kurt Damar; Eisenschmid, Thomas Carl; Packett, Diane Lee; Tjaden, Erik Bruce. Union Carbide Chemicals and Plastics Technology Corp., USA), described conversion of 1,3-butadiene to 3- and 4-pentenols in EtOH in the presence of $Et_3P$ and dicarbonylacetylacetonatorhodium (I) at 80° C. in a stirred reactor under pressure (300 psi H/300 psi CO); g) GB2306344 A1, 1997 May 7, "Hydroformylation process and catalysts for the preparation of linear alcohols from alpha-olefins", (Arnoldy, Peter, Shell Internationale Research Maatschappij BV, Neth.), described preparation of linear alcohols (e.g., 1-dodecanol) by the reaction of alpha-olefins (e.g., 1-undecene) with H2 and CO in the presence of catalyst systems comprising: (A) a source of Group VIIIB metal cations (e.g., a palladium salt); (B) a source of anions other than halide ions (e.g., F3CSO3H); (C) a bidentate ligand [e.g., 1,2-bis(1,4-cyclooctylenephosphino)ethane]; and (D) an alkali or alkali-earth metal iodide (e.g., KI);

There is growing interests in developing mixed catalyst systems to convert olefins to alcohols in "one step". For example, h) WO 2001070660 A1, "Combined hydroformylation and hydrogenation process and catalysts for preparing an alcohol directly from an olefin" (Lange, Jean-Paul, Shell Internationale Research Maatschappij BV, Neth.), described a process for the preparation of an alcohol (e.g., 1-nonanol) from an olefin (e.g., 1-octene) by reacting the olefin with synthesis gas (i.e., H2 and CO) in the presence of a catalyst system comprising a homogeneous hydroformylation catalyst [e.g., palladium acetate and 1,3-bis(dibutylphosphino) propane] and a heterogeneous catalyst comprising copper on a support (e.g., silica); i) U.S. Pat. No. 6,426,437 B1, 2002 Jul. 30, "Hydroformylation and hydrogenation process and catalysts for the manufacture of 1,4-butanediol from allyl alcohol" (Shum, Wilfred P. Arco Chemical Technology, L.P., USA), described preparation of 1,4-Butanediol by hydroformylating allyl alcohol in the presence of a solvent and a catalyst system comprising a rhodium complex, a ruthenium complex, and a diphosphine ligand, and hydrogenating the resulting 4-hydroxybutyraldehyde using the same catalyst system. This process gives high yields of 1,4-butanediol when compared to the 2-methyl-1,3-propanediol byproduct.

There is a need to develop homogeneous aldehyde hydrogenation catalysts that are compatible with more selective hydroformylation catalysts to produce alcohols from olefins in the same reactor under mild low pressure oxo conditions. The most studied homogeneous aldehyde hydrogenation catalysts are ruthenium and rhodium systems. Both ruthenium and rhodium catalysts, however, suffer from the need of very high temperatures and pressures and/or slow rate of hydrogenation. $RuC_{12}(CO)_2(PPh_3)2$, for example, was reported (Walter Strohmeier and Luise Weigelt, Journal of Organometallic Chemistry, 145 (1978) 189–194) to hydrogenate butanal with 3840 turnover/hour rate at 160° C. and 15 atmosphere hydrogen. The selectivity to butanol was only 87% due to formation of heavier by-products from aldol condensation reactions. The same catalyst was reported (Sanchez-Delgado, R. A.; Andriollo, A.; De Ochoa, O. L.; Suarez, T.; Valencia, N. Journal of Organometallic Chemistry (1981), 209(1), 77–83) to have a very slow propionaldehyde hydrogenation rate of 67 turnovers/hour at 80° C. and 30 atmosphere of hydrogen, with even lower selectivity (67%) for propanol. In the same article, $RuHCl(PPh_3)_3$ was reported to be a much better catalyst for propionaldehyde hydrogenation with a rate of 653 turnovers/hour under the same conditions. Replacing a triphenylphosphine from $RuHCl(PPh_3)_3$ with a CO reduced the catalyst activity to about 50%. The most effective rhodium catalysts for aldehyde hydrogenation are rhodium complexes of tri-n-alkylphosphines. A cationic rhodium complex of triethylphosphine, for example, was reported (Fujitsu, Hiroshi; Matsumura, Eiichi; Takeshita, Kenjiro; Mochida, Isao. Journal of Organic Chemistry (1981), 46(26), 5353–7) to hydrogenate n-butanal at 30° C. and one atmosphere hydrogen with a rate of 31 turnovers/hour. Both catalyst systems in EP420510A2 and WO9739995A1 cited hereinabove comprised of aldehyde hydrogenation catalysts although the structures of the catalysts have not been fully identified. Both systems required high temperature and high syn gas pressure to achieve acceptable rate of reactions.

SUMMARY OF THE INVENTION

This invention comprises a process for hydrogenation of aldehydes to alcohols using novel homogeneous catalysts. The catalysts are generated in situ under hydrogen and carbon monoxide gases in a suitable solvent, by mixing a rhodium catalyst precursor, such as $Rh(CO)_2$ acetoacetonate, and a ligand of formula I.

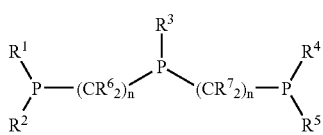

Formula I

Wherein
Preferably, n is 3 to 5;
$R^1$, $R^2$, $R^3$, $R^4$ and $R^5$ are hydrocarbyl radicals;
$R^1$ and $R^2$ can be linked, together with P, to make a five to seven numbered ring, and $R^4$ and $R^5$ can be linked, together with P, to make a five to seven numbered ring;
Each $R^6$ is individually an alkyl, aryl, or hydrogen radical. Any two $R^6$ groups can be linked to make a five to seven numbered ring.
Each $R^7$ is individually an alkyl, aryl, or hydrogen radical. Any two $R^7$ groups can be linked to make a five to seven numbered ring.
More preferably, n is 3, $R^1$, $R^2$, $R^3$, $R^4$ and $R^5$ are alkyl or aryl radicals. $R^6$ and $R^7$ are hydrogen radicals.

DETAILED DESCRIPTION OF THE PREFERRED EMBODIMENTS

Figure 1:
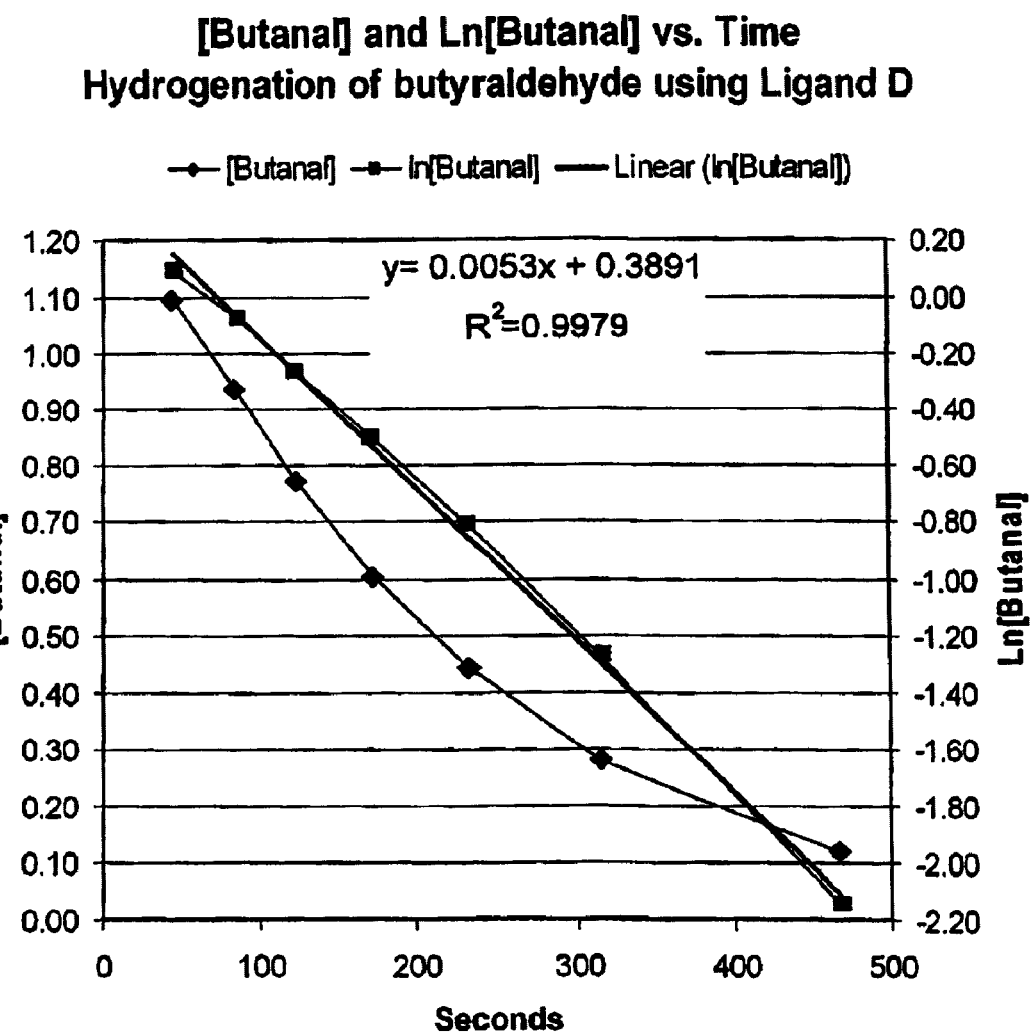
FIG. 1 is a graph of concentration of butanal and natural log of such concentration versus time for an example of the reaction of this invention.

This invention comprises a process for hydrogenation of aldehydes to alcohols using novel homogeneous catalysts. The catalysts are generated in situ under hydrogen and carbon monoxide gases in a suitable solvent, by mixing a rhodium catalyst precursor, such as $Rh(CO)_2$acetoacetonate, and a ligand of formula I.

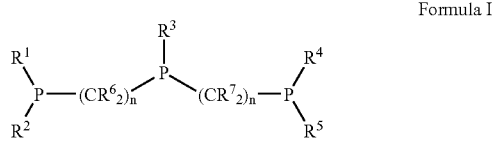

Formula I

Wherein
Preferably, n is 3 to 5;
$R^1$, $R^2$, $R^3$, $R^4$ and $R^5$ are hydrocarbyl radicals;
$R^1$ and $R^2$ can be linked, together with P, to make a five to seven numbered ring, and $R^4$ and $R^5$ can be linked, together with P, to make a five to seven numbered ring;
Each $R^6$ is individually an alkyl, aryl, or hydrogen radical. Any two $R^6$ groups can be linked to make a five to seven numbered ring.
Each $R^7$ is individually an alkyl, aryl, or hydrogen radical. Any two $R^7$ groups can be linked to make a five to seven numbered ring.
More preferably, n is 3, $R^1$, $R^2$, $R^3$, $R^4$ and $R^5$ are alkyl or aryl radicals. $R^6$ and $R^7$ are hydrogen radicals.

Preferred embodiments of the ligand of Formula I are listed hereinbelow:

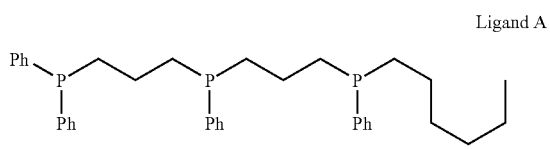

Ligand A

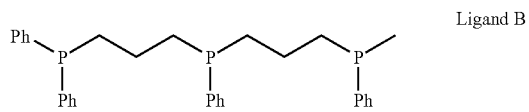

Ligand B

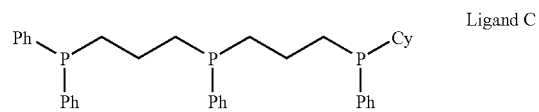

Ligand C

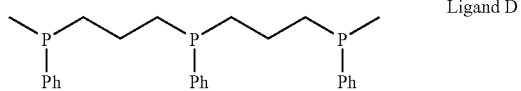

Ligand D

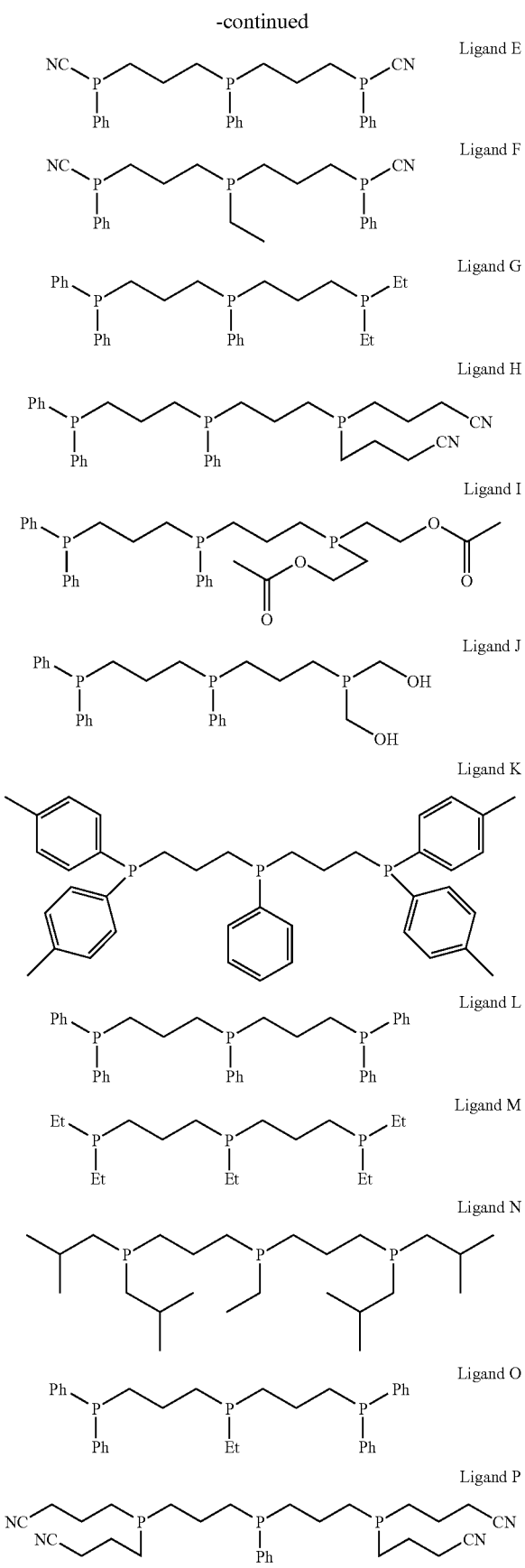

Thus, as can be seen from the preceding preferred embodiments of the ligand of Formula I, "hydrocarbyl" as used herein is to be considered to include organic groups that further contain one or more heteroatoms.

The aldehyde hydrogenation reactions can be carried out in any suitable solvents that do not interfere with the hydrogenation catalysts. Suitable solvents include, but are not limited to, ethers, such as diethyl ether and tetrahydrofuran, alcohols, such as methanol, ethanol, 1-propanol, 2-propanol, butanol pentanol, hexanol, heptanol, octanol and nonanol, aromatics, such as toluene and alkanes, such as hexane. A mixture of solvents can also be used and is preferred for most catalysts. Water can be present in the reaction solution for some of the ligands. Alcohol solvents have activity enhance effects. However, using too high a concentration of an alcohol may lead to Aldol condensation of the aldehyde when a very electron-rich ligand is used. The optimum concentration of an alcohol depends on the electronic property of the ligand and the property of the alcohol. Generally, the alcohol concentration is less than 8 mol/L. It is not necessary to start a reaction with an alcohol, because the process produces alcohols. The preferred operation is to start with a low concentration of the product (alcohol) in the reactor.

The aldehyde hydrogenation reaction can be carried out, preferably, from 25° C. to 150° C., more preferably, 35° C. to 120° C., and most preferably, 45° C. to 100° C.

The hydrogen partial pressure is, preferably, from 1 psi to 2000 psi, more preferably, 10 psi to 1500 psi, and most preferably 30 psi to 1000 psi.

The carbon monoxide partial pressure is, preferably, from 1 psi to 2000 psi, more preferably, 10 psi to 1200 psi, and most preferably 20 psi to 1000 psi.

Aldehyde can be added to the reaction solution or generated in situ from an olefin using a hydroformylation catalyst promoted by a bis-chelating phosphorus ligand, for example, hydroformylation ligand T and U.

Ligand T

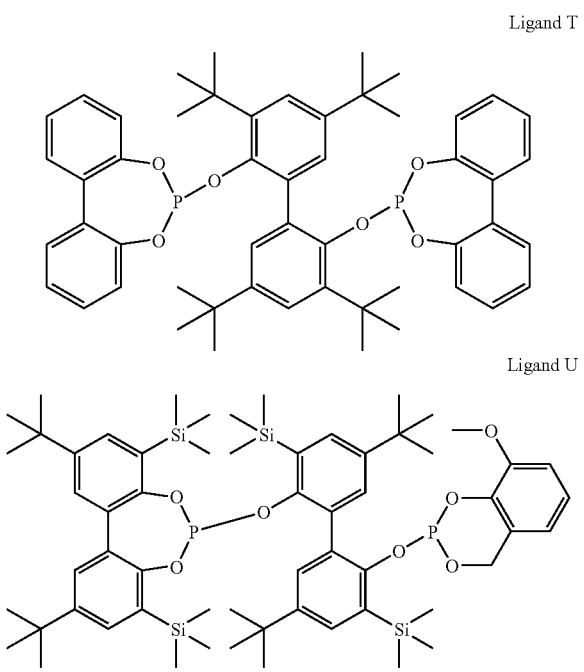

Ligand U

A reaction is referred to reductive hydroformylation when an olefin is converted directly to alcohols using a mixed catalyst system, which comprises a rhodium complex of a ligand selected from Ligand A through Ligand S and rhodium complex of ligand T, ligand U, or any other bis-chelating phosphorus ligand.

Ligand Synthesis

Another aspect of the invention comprises synthetic routes to make ligands with desired electronic and steric properties. Two of the ligands, Ligand L and Ligand M, are known in the literature. Ligand M was synthesized by photolyzing with 365 nm UV a mixture of diethylphosphine and diallylethylphosphine in the presence of catalytic amount of 2,2'azobisisobutyronitrile (AIBN) (Süssmilch, F. et al. *J. of Organometallic Chem.* 1990, 388, 95–10, see Synthetic Scheme 1). Ligand F, Ligand N and Ligand O were synthesized similarly using cyanoethylphenylphosphine, diisopropylphosphine and diphenylphosphine with diallylethylphosphine, respectively. Ligand M and ligand N are very electron rich, forming catalysts that are very sensitive to water and incompatible with hydroformylation catalysts.

Synthetic Scheme 1

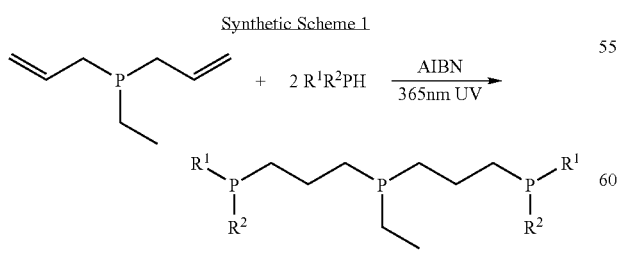

Synthesis of Ligand L was reported by Green, L. M. and Meek, D. W. (*Polyhedron* 1990, Vol. 9, No. 1, pp. 35–45, see Synthetic Scheme 2). The first step of this synthetic route produces bis(3-chloropropyl)phenylphosphine by reacting 1-bromo-3-chloropropane selectively with organophosphides (PhHPLi and Ph(3-chloropropyl)PLi) generated in situ using lithium N,N-diisopropylethylamine and phenylphosphine at low temperature. The second step involves reacting bis(3-chloropropyl)phenylphosphine with two equivalents of a lithium diorganophosphide, again, generated in situ at low temperature. Both steps produce the desired products in greater than 95% yield. Ligand D, K, and S were also synthesized using this route. Ligand L is very electron deficient and very bulky, forming a catalyst that has low activity. Ligand D formed the most active aldehyde hydrogenation catalyst.

Synthetic Scheme 2

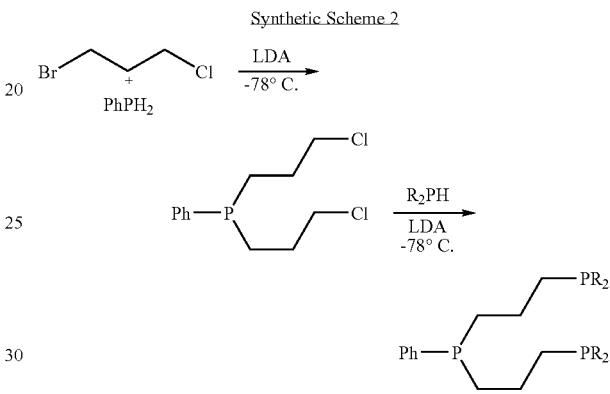

Green and Meek also reported (in the article cited hereinabove) a stepwise synthetic route (Scheme 3) to unsymmetrical triphosphines, which was employed to synthesize Ligand A, B and C.

Synthetic scheme 3:

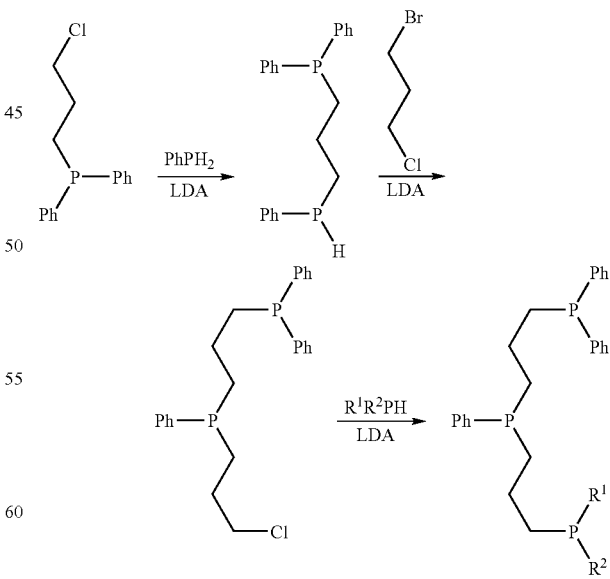

The chemistry shown in Scheme 1 and Scheme 3 can also be combined to synthesize some of the ligands. Ligand G, for example, was synthesized following Scheme 4.

Synthetic scheme 4:

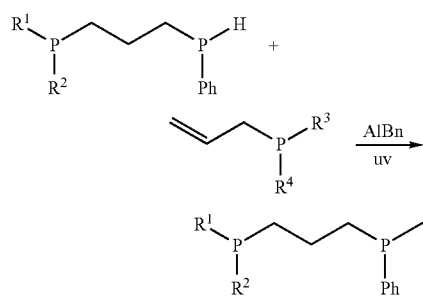

Although the synthetic schemes 1, 2, 3 and 4 described above provide efficient route to many triphosphine ligands, all these syntheses rely on the use of primary and secondary phosphines. Two new synthetic routes (Synthetic Scheme 5 and 6) have been invented to synthesize new ligands. The new routes make it possible to make ligands that are difficult or impossible to make using Schemes 1 through 4. The common intermediates that bear the primary terminal phosphine(s) are synthesized by following the chemistry reported by Bampos, N. Field, L. D. Messerle, B. A. and Smemik, R. J. *Inorg. Chem.* 1993, 32, 4084–4088. Ligand P, Q and R were synthesized using scheme 5 and Ligand H, I and J were synthesized using scheme 6.

Synthetic Scheme 5

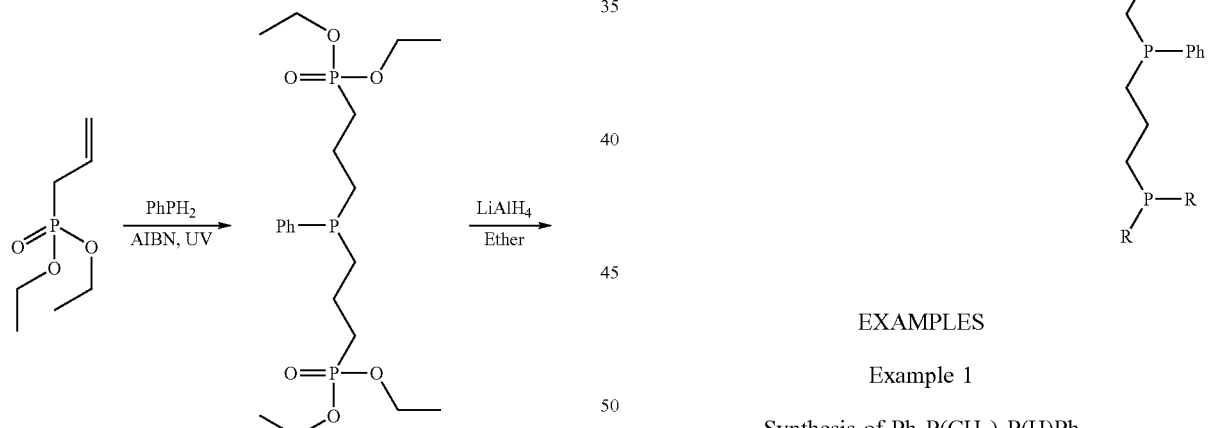

-continued
Synthetic Scheme 6

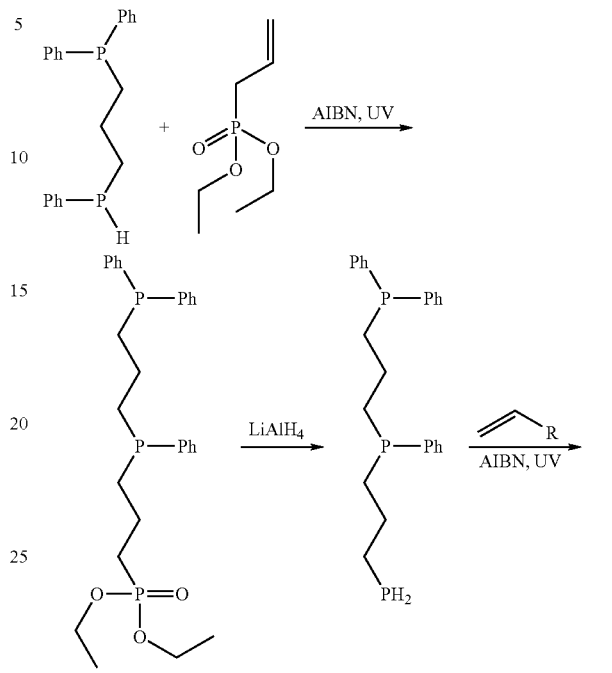

EXAMPLES

Example 1

Synthesis of $Ph_2P(CH_2)_3P(H)Ph$

In a Schlenk flask were placed phenylphosphine (3.3806 g, 30.71 mmol) with THF (60 ml) and chilled to −30° C. in a freezer over 30 minutes. To this solution was added lithium diisopropylamide (16 ml, 32.16 mmol) and the resulting solution was allowed to warm to room temperature while stirring. In a 250 ml Schlenk flask was placed $(C_6H_5)_2P(CH_2)_3Cl$ (7.9089 g, 30.1 mmol) in 100 ml THF and the solution was cooled to −78° C. The lithium phenylphosphide solution was added to the $(C_6H_5)_2P(CH_2)_3Cl$ solution at such a rate that the temperature of the solution remained constant at −78° C. After addition, the solution was slowly warmed to room temperature. Degassed DI water (0.2 ml) was added to the dark orange solution. The color changed to yellow-orange. The solvents were removed in vacuo. The resulting gel was dissolved in toluene and filtered through Celite. Toluene was then removed in vacuo, leaving an orange-yellow oil. Yield: 10.0 g (99.1%). $^{31}P\{^1H\}$ NMR (CDCl$_3$, 122 MHz, δppm: −16.30 and −52.86 (>99% pure). $^1H$ NMR (CDCl$_3$, 400 MHz, δ: 1.58–2.15 (3 complex peaks integrated to ~7Hs), 4.12 (d of t, H—P) and 7.26–7.43 (complex pattern).

Example 2

Synthesis of $(C_6H_5)_2P(CH_2)_3P(C_6H_5)(CH_2)_3Cl$

A solution of $(C_6H_5)_2P(CH_2)_3P(H)(C_6H_5)$ (10.0 g, 29.7 mmol), tetrahydrofuran (100 ml) and 1-Bromo-3-chloropropane (5.086 g, 32.3 mmol) was prepared in a Schlenk flask and cooled to −78° C. Using a cannula, lithium diisopropylamide (16.6 ml, 33.0 mmol) was added dropwise at a rate such that the temperature was held constant. The resulting solution was warmed to room temperature and stirred for 30 minutes. Degassed, DI water (0.2 ml) was added to quench any unreacted lithium reagents. The solvents were removed in vacuo without heat. The resulting orange gel was stirred in toluene (200 ml) and filtered through a medium fritted glass funnel packed with Celite. The filtrate was then removed in vacuo with a room temperature water bath, leaving an orange oil containing fine solids. The material was again stirred in toluene and filtered through Celite. The solvent was then removed in vacuo with a room temperature water bath to obtain a viscous orange oil. Yield: 11.7 g 95.7%. $^{31}P\{^1H\}$ NMR (CDCl$_3$, 122 MHz, δppm: −16.66 and −26.17 (>96% pure).

Example 3

Synthesis of Ligand A, $Ph_2P(CH_2)_3P(Ph)(CH_2)_3P(Ph)(n-C_6H_{13})$

This reaction was carried out in a glove box. A solution of cyclohexylphenylphosphine (2.023 g 10.41 mmol) and tetrahydrofuran (30 ml) was cooled to −30° C. for 30 minutes. Lithium diisopropylamide (5.6 ml, 11 mmol) was added to the cooled solution and allowed the resulting solution to warm to room temperature with an additional hour of stirring. In a separate flask, $(C_6H_5)_2P(CH_2)_3P(C_6H_5)(CH_2)_3Cl$ (4.3605 g, 10 mmol) was dissolved in 60 ml THF and chilled to −30° C. over 30 minutes. Using a syringe, the lithium cyclohexylphenylphosphide solution was added to the $(C_6H_5)_2P(CH_2)_3P(C_6H_5)(CH_2)_3Cl$ solution at −30° C. This dark orange solution was stirred overnight. Ethanol (0.2 ml) was then added to the solution. The solution turned orange yellow in color. Solvents were removed in vacuo and the residue stirred in toluene and filtered through a medium fritted glass funnel packed with Celite. The filtrate was contained in a Schlenk flask, brought out of the glove box and washed twice with degassed DI water (50 ml). The toluene layered was dried over MgSO$_4$ for 30 minutes and then brought back into the box and filtered. The volume was reduced to approximately 15 ml under vacuum and then heated under vacuum to remove trace amount of monophosphines, giving an orange oil. Yield: 4.20 g 73.5%. $^{31}P\{^1H\}$ NMR (CDCl$_3$, 122 MHz, δppm: Ph$_2$PCH$_2$—: −16.38; —CH$_2$P(Ph)CH$_2$— −25.26, and −25.30; and —CH$_2$P(Me)Ph: −26.46 (>96% pure).

Example 4

Synthesis of Ligand B, $Ph_2P(CH_2)_3P(Ph)(CH_2)_3P(Ph)Me$

Ligand B was synthesized by following the same procedure as describe in example 3 using $(C_6H_5)_2P(CH_2)_3P(C_6H_5)(CH_2)_3Cl$ (4.39 g, 10.6 mmol), Phenylmethylphosphine (1.4551 g, 11.72 mmol), lithium diisopropylamide (LDA, 6.0 ml, 12.0 mmol) and tetrhydorfuran (60 ml). Yield: 2.94 g (58.7%). $^{31}P\{^1H\}$ NMR (CDCl$_3$, 122 MHz, δ ppm: Ph$_2$PCH$_2$—: −16.56; —CH$_2$P(Ph)CH$_2$— −26.13; and —CH$_2$P(Me)Ph: −35.97 and −36.04 (>96% pure).

Example 5

Synthesis of Ligand C, $Ph_2P(CH_2)_3P(Ph)(CH_2)_3P(Ph)Cy$

The procedure for the Synthesis of HexPh$_4$P$_3$Pr above was followed using $(C_6H_5)_2P(CH_2)_3P(C_6H_5)(CH_2)_3Cl$ (1.73 g, 4.15 mmol), Phenylcyclohexylphosphine (1.01 g, 6.81 mmol) and lithium diisopropylamide (4.4 ml, 8.8 mmol). Yield: 1.89 g (81.4%). $^{31}P\{^1H\}$ NMR (CDCl$_3$, 122 MHz, δppm: —CH$_2$P(Cyhex)Ph: −11.67 and −11.79; Ph$_2$PCH$_2$—: −16.52; —CH$_2$P(Ph)CH$_2$— −26.21 and 26.34 (>98% pure).

Example 6

Synthesis of ligand D, $PhP[(CH_2)_3P(Ph)Me]_2$

PhP[(CH$_2$)$_3$Cl]$_2$ (3.48 g, 13.2 mmol) and methylphenylphosphine (3.916 g (90% tech grade, 28.4 mmol) dissolved in 30 ml THF and the solution was cooled to −35° C. LDA (15.78 g, 1.5 M solution, 29.00 mmol) was added to the cold solution dropwise. The solution was stirred for 2 hours at ambient temperature. The solvents were then removed under vacuum to obtain a yellow viscous oil. Toluene (80 ml) was added to dissolve the product. Water (70 ml) was added and the resulting mixture stirred for 10 minutes. The organic phase was then transferred into a flask containing MgOS$_4$ under nitrogen. The aqueous phase was extracted with toluene (3×20 ml) and the toluene extracts were combined. The toluene solution was then filtered in a glove box and the filtrated evaporated to obtain a yellow viscous oil. The oil was dissolved in about 10 ml pentane and the resulting solution placed in the freezer at −35° C. An oil layer formed. The supernatant was decanted and the oil was washed with 5 ml pentene twice and then dried under vacuum to obtain 5.06 g (85.2%) desired ligand as an viscous oil with about 97% purity. $^{31}P\{^1H\}$ NMR (CDCl$_3$, 122 MHz, δ ppm: −25.815 (s, 2Ps); −35.948 and −36.020 (s, 1P each). $^1H$ NMR (CDCl$_3$, 300 MHz, δ: 7.514 to 7.364 (complex pattern, 15 H's on the Phenyls); 1.815 and 1.543 (9 and 7 line patterns, respectively, 8Hs and 4Hs, —PCH$_2$CH$_2$CH$_2$P—).

Example 7

Synthesis of ligand E, $[(NCCH_2CH_2)PhP(CH_2)_3]_2PPh$

Ligand E was synthesized by following the procedure described in example 6. $^{31}P\{^1H\}$ NMR (122 Mhz, CDCl$_3$, δ, ppm): Internal P: −26.7 (t). Terminal P: −24.5 (s).

Example 8

Synthesis of ligand F, [(NCCH$_2$CH$_2$)PhP(CH$_2$)$_3$]$_2$PEt

Photolysis using a UV (365 nm) lamp of cyanoethylphenylphosphine (3.59 g, 22 mmol) and ethyldiallylphosphine (1.42 g, 10.0 mmol) with 10 mg AIBN for 22 hours produced the desired ligand. The ligand was purified by washing with hexane and dried under vacuum. Isolated yield: 4.1 g (88%). $^{31}$P{$^1$H} NMR (122 Mhz, CDCl$_3$, δ, ppm): Internal P: −28.0, −28.4 and −28.5. Terminal P: −24.1, −24.2 and −24.4.

Example 9

Synthesis of ligand G, Ph$_2$P(CH$_2$)$_3$P(Ph)(CH$_2$)$_3$PEt$_2$

Ph$_2$P(CH$_2$)$_3$P(H)Ph (3.68 g, 10.9 mmol), allyldiethylphosphine (1.71 g, 13.1 mmol) and AIBN (0.011 g) were mixed in a Schlenk flask and radiated with a 365 nm UV lamp for 20 hours. After confirming that the reaction was complete by $^{31}$P NMR analysis, it was distilled under vacuum (<0.5 mm Hg) at a final heating mantle temperature of 210° C. for an hour to remove impurities. The ligand remained in the pot. Yield: 3.36 g (66%). $^{31}$P NMR (122 MHz, CDCl$_3$, δ, ppm): −16.74 (s), −23.09 (s) and −25.98 (s). There are peaks near the three major peaks, which have not been determined if are part of the ligand or due to impurities. $^1$H NMR (500 MHz, CDCl$_3$, δ, ppm): 1.001 (d of q, J$_{H-P\&H}$=7.0 Hz 4H's methylenes of ethyl groups), 1.3 to 2.2 (m, H's on methyls and propylenes) (d of t, J$_{H-P\&H}$=211 & 6.6 Hz, H on the P), and 7.30 to 7.47 (m, 15H's on phenyl rings).

Example 10

Synthesis of Ph$_2$P(CH$_2$)$_3$(Ph)P(CH$_2$)$_3$PH$_2$

Diethyl allylphosphonate (20.00 g, 112.3 mmol), Ph$_2$P(CH$_2$)$_3$PH(Ph) (16.00 g, 47.3 mmol) and 2,2'-azobisisobutyronitrile (0.005 g, 0.03 mmol) were mixed in a Schlenk tube with a magnetic stir bar under nitrogen. The solution was irradiated with a UV (365 nm) lamp with stirring for 36 hours. After removing excess diethyl allylphosphonate under reduced pressure, 21.93 g (89.5% yield) viscous amber oil was obtained. This viscous oil was dissolved in 200 ml ether and the resulting solution was dropwise added into an ether (300 ml) suspension of LiAlH$_4$ (5.67 g, 149 mmol) at 0° C. with stirring. The mixture was then stirred at ambient temperature for 2 hours. A sample (~2 ml) was taken from the flask and worked up to make a NMR sample, which showed 100% conversion to the desired product. The flask was then cooled to 0° C. with an ice bath. Water (200 ml) added slowly into the flask (Caution: very exothermic and producing hydrogen gas!). The organic layer was transferred into a flask under nitrogen containing MgSO$_4$. The white gel/slurry was washed with ether (3×100 ml) and the ether washes were combined with the first organic layer. The flask was brought into a glove box to filter the MgSO$_4$. The filtrate was evaporated to obtain 8.0 g (46%) yellow oil. Further extraction recovered another 4.6 g product with a 65% total yield form Ph$_2$P(CH$_2$)$_3$PH(Ph). $^{31}$P{$^1$H} NMR (CDCl$_3$, 122 MHz, δ ppm: −16.670, −25.883 and −137.829 (s, 1 P each) (>99% pure with a small peak at −52.968 <1 mol %). $^1$H NMR (CDCl$_3$, 300 MHz, δ: 7.507 to 7.268 (complex pattern, 15 H's on the Phenyls); 2.644(d of t, J$_{H-P}$=195 Hz and J$_{H-H}$=7.5 Hz, 2 H's on the P); 2.193 to 1.479 (complex, 12H's on the two PCH$_2$CH$_2$CH$_2$P). The $^1$H NMR also showed that the product contained 6.5 mol % diethyl ether.

Example 11

Synthesis of ligand H, Ph$_2$P(CH$_2$)$_3$(Ph)P(CH$_2$)$_3$P[(CH$_2$)$_3$CN]$_2$ Ph$_2$P(CH$_2$)$_3$(Ph)P(CH$_2$)$_3$PH$_2$ (1.00 g, 2.44 mmol), allyl cyanide (0.500 g, 7.46 mmol), AIBN (5 mg, 0.03 mmol) and toluene (1.0 g) were stirred and irradiated (365 nm) for about 16 hours in a vial with stirring. The vial was then brought into a box and the solvent evaporated. Residual oil was stirred in 10 ml ether, cooled to −35° C. and then decanted. The residual oil was dried in the vacuum chamber of a glove box. Yield: 0.99 g (74%). $^{31}$P{$^1$H} NMR (CD$_3$CN, 122 MHz, δ ppm: −16.664, −26.321 and −33.282 (s, 1P each) (~95% pure). $^1$H NMR (CD$_3$CN, 300 MHz, δ: 7.491 to 7.165 (complex pattern, 15 H's on the Phenyls); 2.430 (q, J$_{H-HP}$=7.2 Hz, 4 H's on the PCH$_2$CH$_2$CH$_2$CN); 2.348 to 1.177 (complex, 12 H's on the two PCH$_2$CH$_2$CH$_2$P and 8 H's on PCH$_2$CH$_2$CH$_2$CN).

Example 12

Synthesis of ligand I, Ph$_2$P(CH$_2$)$_3$(Ph)P(CH$_2$)$_3$P[(CH$_2$)$_2$OC(O)CH$_3$]$_2$ Ph$_2$P(CH$_2$)$_3$(Ph)P(CH$_2$)$_3$PH$_2$ (2.04 g, 4.98 mmol), vinyl acetate (1.92 g, 15.0 mmol), AIBN (5 mg, 0.030 mmol) and THF (2.0 g) were stirred and irradiated with a UV lamp (365 nm) for about 16 hours in a vial with stirring. The vial was brought into a box and the solvent and excess vinyl acetate evaporated. Residual oil was stirred in 10 ml pentane, cooled the mixture to −35° C. and then pentane was decanted. This procedure was repeated twice and the oil remained in the vial was pumped in the vacuum chamber of a glove box to yield 2.6 g (90%) product. $^{31}$P{$^1$H} NMR (CDCl$_3$, 122 MHz, δ ppm: −17.662, −27.161 and −40.041 (s, 1P each) (~96% pure). $^1$H NMR (CDCl$_3$, 300 MHz, δ: 7.445 to 7.261 (complex pattern, 15H's on the Phenyls); 4.162 (quintet, J$_{H-H,P}$=7.5 Hz, 4H's on the —PCH$_2$CH$_2$O—); 2.122 (9 line pattern, J$_{H-H}$=7.5 Hz, 4H's on PCH$_2$CH$_2$OC(O)CH$_3$); 2.028 (s, 6H's —COCH$_3$); 1.874 to 1.472 (complex, 12H's on the two PCH$_2$CH$_2$CH$_2$P).

Example 13

Synthesis of ligand J, Ph$_2$P(CH$_2$)$_3$(Ph)P(CH$_2$)$_3$P(CH$_2$OH)$_2$

Ph$_2$P(CH$_2$)$_3$(Ph)P(CH$_2$)$_3$PH$_2$ (1.02 g, 2.48 mmol), formaldehyde (0.600 g 37 wt % water solution, 7.5 mmol), and 1-propanol (5.0 ml) were stirred at ambient temperature for about 16 hours in Schlenk flask with stirring. Acetic acid (1.0 g) was then added into the reaction solution and the solution was heated to 60° C. Solvents were then removed by sparging nitrogen through the solution. The resulting oil was dissolved in 10 ml methanol, heated to 60° C. Solvents were again removed by sparging nitrogen through the solution. The vial was then brought into a box and the oil was dried in the vacuum chamber of a glove box. Yield: 1.19 g (100%). $^{31}$P{$^1$H} NMR (CD$_3$OD, 122 MHz, δ ppm: −16.248, −24.819 and −25.416 (s, 1P each) (~97% pure). $^1$H NMR (CD$_3$OD, 300 MHz, δ: 7.465 to 7.263 (complex pattern, 15 H's on the Phenyls); 4.856 (s, 2H on the hydroxyls); 3.917(d of d, $J_{H\text{-}HP}$=6.9 and 5.1 Hz, 4 H's on the PCH$_2$OH); 2.123 to 1.381 (complex, 12 H's on the two PCH$_2$CH$_2$CH$_2$P).

Example 14

Synthesis of ligand K, PhP[(CH$_2$)$_3$P-(p-CH$_3$C$_6$H$_4$)$_2$]$_2$

This ligand was synthesized by following the procedure described in Example 6, using PhP[(CH$_2$)$_3$Cl]$_2$ (1.00 g, 3.80 mmol), di-p-tolylphosphine (1.73 g, 7.98 mmol), THF (20 ml) and LDA (5.68 g 1.5 M solution, 10.40 mmol). Similar workup yielded 2.18 g (51.8%) desired ligand as an viscous oil with about 95% purity. $^{31}$P{$^1$H} NMR (CDCl$_3$, 122 MHz, δ ppm: −18.618 (s, 2Ps); −26.073 (s, 1P). $^1$H NMR (CDCl$_3$, 300 MHz, δ: 7.316 to 7.112 (complex pattern, 21 H's on the Phenyl and p-Tolyls); 2.337 (s, 12Hs on the methyls of p-tolyls); 2.078, 1.804 and 1.500 (8, 8, and 7 line patterns, respectively, 4Hs each, —PCH$_2$CH$_2$CH$_2$P—).

Example 15

Synthesis of Ligand L, PhP[(CH$_2$)$_3$PPh$_2$]$_2$

PhP[(CH$_2$)$_3$PPh$_2$]$_2$ is a known compound and was synthesized according to the literature procedures (see Scheme 2 hereinabove). $^{31}$P{$^1$H} NMR (122 Mhz, CDCl$_3$, δ, ppm): Internal P: −26.7 (s). Terminal P: −16.8 (s).

Example 16

Synthesis of ligand M, EtP[(CH$_2$)$_3$PEt$_2$]$_2$

EtP[(CH$_2$)$_3$PEt$_2$]$_2$ is a known compound and was synthesized according to literature procedures. Diallyethylphosphine (3.15 g, 22.2 mmol), diethylphosphine (5.30 g, 58.8 mmol) and azobisisobutylnitrile (AIBN, 0.010 g, 0.06 mmol) were mixed in a Schlenk flask with a stir bar and radiated with a 365 nm UV lamp for 5 days. The reaction solution was then distilled under vacuum using a short path trap-to-trap apparatus with the receiver cooled in liquid nitrogen. This was only to remove the unreacted diethylphosphine and some impurities. The final heating mantle temperature was 180° C. and the vacuum was about 0.5 mmHg. The product remained in the pot. Yield: 3.16 g, 44%. $^{31}$P NMR (122 MHz, CDCl$_3$, δ, ppm): −22.76 (s, terminal P's) and −27.38 (s, central P). $^1$H NMR (300 MHz, CDCl$_3$, δ, ppm): 1.0006 (d of t, $J_{H\text{-}H\&P}$=8.1 Hz, H's on methyl groups) and 1.312 to 1.573 (m, H's on methylene groups).

Example 17

Synthesis of Ligand N, EtP[(CH$_2$)$_3$P(i-Bu)$_2$]$_2$

This ligand was synthesized and isolated by following the same procedure as described in Example 16, except that diisobutylphosphine was used in place of diethylphosphine. Yield: 50%. $^{31}$P NMR (122 MHz, CDCl$_3$, δ, ppm): −22.34 and −27.39 (s, central P), and −39.41 (s, terminal P's). It is not clear why two peaks were in the spectrum for the central phosphorus atom. $^1$H and $^{13}$C NMR spectra showed that the product was quite pure. $^1$H NMR (300 MHz, CDCl$_3$, δ, ppm): 0.973 (d, $J_{H\text{-}H\&P}$=6.6 Hz, 24 H's on methyls of isobutyl groups) and 1.660 (nonanet, $J_{H\text{-}H\&P}$=6.6 Hz, H's on the tertiary carbon atoms of isobutyl groups). Peaks for protons on the ethyl and propylenes are not assigned from 1.008 to 1.55. $^{13}$C NMR (126 MHz, CDCl$_3$, δ, ppm): 9.56 (d, 1 C, methyl of ethyl), 19.19 (d, 1 C, methylene of ethyl), 22.45 (t, 2 C's, center carbon atoms of the propylenes), 24.34 (t, 8 C's, methyls of isobutyls), 26.45 (d, 4 C's, methylenes of isobutyls), 28.62 (d of d, 2 C's, P-bound C's of propylenes), 30.82 62 (d of d, 2 C's, P-bound C's of propylenes), and 39.21 (d, 4 C's, tertiary carbon atoms of isobutyls).

Example 18

Synthesis of ligand O, EtP[(CH$_2$)$_3$PPh$_2$]$_2$

This ligand was synthesized and isolated by following the same procedure as described in Example 16, except that diphenylphosphine was used in place of diethylphosphine. Yield: 46%. $^{31}$P NMR (122 MHz, CDCl$_3$, δ, ppm): −16.55 (s, terminal P's) and −28.53 (s, central P). There are also two peaks at −17.11 and −28.04, which are about 12% of the major peaks. $^1$H NMR (300 MHz, CDCl$_3$, δ, ppm): 0.969 (d of t, $J_{H\text{-}H\&P}$=6.6 Hz, H's on methyl of ethyl), 1.296 (q, $J_{H\text{-}H\&P}$=6.6 Hz, H's on methylene of ethyl), 1.437 to 2.206 (m, H's on propyls) and 7.256 to 7.445 (m, H's on phenyls).

Example 19

Synthesis of PhP[(CH$_2$)$_3$P(O)(OC$_2$H$_5$)$_2$]$_2$

Diethyl allylphosphonate (30.00 g, 168.4 mmol), phenylphosphine (8.340 g, 75.77 mmol) and 2,2'-azobisisobutyronitrile (0.030 g, 0.18 mmol) were mixed in a Schlenk tube with a magnetic stir bar under nitrogen. The solution was irradiated with a UV (365 nm) lamp with stirring for 36 hours. After removing excess diethyl allylphosphonate under reduced pressure, 32.73 g (92.6% yield) viscous slightly yellow oil was obtained. $^{31}$P{$^1$H} NMR (CDCl$_3$, 122 MHz, δ ppm: 31.82 and −26.63 (>96% pure). $^1$H NMR (CDCl$_3$, 400 MHz, δ: 7.30 to 7.13 (complex pattern, 5 H's on the Phenyl); 3.84 (complex pattern, 8 H's on the OCH$_2$CH$_3$ groups), 1.64 to 1.55 (complex, 12 H's on the two —CH$_2$CH$_2$CH$_2$—) and 1.06 (t of d, $J_{H\text{-}H}$=6.9 Hz and $J_{H\text{-}P}$=4.2 Hz, 12 H's on the OCH$_2$CH$_3$ groups).

Example 20

Synthesis of PhP[(CH$_2$)$_3$PH$_2$]$_2$

PhP[(CH$_2$)$_3$P(O)(OC$_2$H$_3$)$_2$]$_2$ (33.00 g, 70.8 mmol) was dissolved in 150 ml ether and the resulting solution was dropwise added into an ether (350 ml) suspension of LiAlH$_4$ (21.5 g, 566 mmol) at 0° C. with stirring. The mixture was then stirred at ambient temperature for 15 hours. A sample (~2 ml) was taken from the flask and worked up to make a NMR sample, which show 100% conversion to the desired product. The flask was then cooled to 0° C. with an ice bath. Water (200 ml) added slowly into the flask (Caution: very exothermic and producing hydrogen gas!), followed by 15 wt % NaOH in water (125 ml), toluene (125 ml) and water (200 ml). The organic layer was transferred into a flask under nitrogen containing MgSO$_4$. The white gel/slurry was washed with ether (3×120 ml) and the ether washes were combined with the first organic layer. The flask was brought into a glove box to filter the MgSO$_4$. The filtrate was evaporated to obtain 10.6 g (57.9%) yellow oil. $^{31}P\{^1H\}$ NMR (CDCl$_3$, 122 MHz, δ ppm: −25.26 (s, 1 P) and −138.16 (s, 1P) (>99% pure with a small peak at −52.29 <1 mol %). $^1$H NMR (CDCl$_3$, 500 MHz, δ: 7.427 (t, $J_{H-H}$=7 Hz, 2H's on the Phenyl); 7.273 (complex pattern, 3H's on the Phenyl); 2.565 (d of t, $J_{H-P}$=194 Hz and $J_{H-H}$=7.5 Hz, 4 H's on the P's); 1.708 to 1.481 (complex, 12 H's on the two —CH$_2$CH$_2$CH$_2$—). The $^1$H NMR also showed that the product contained 18.6 wt % toluene. So the pure product yield was 46%. The remaining product was trapped in the white gel/slurry.

Example 21

Synthesis of ligand P, PhP[(CH$_2$)$_3$P((CH$_2$)$_3$CN)$_2$]$_2$

PhP[(CH$_2$)$_3$PH$_2$]$_2$ (0.300 g, 1.2 mmol), ally cyanide (0.47 g, 7.0 mmol), AIBN (2 mg, 0.012 mmol) and toluene (0.7 g) were stirred and irradiated (365 nm) for about 16 hours in a vial with stirring. The vial was then brought into a box and the solvent evaporated. Residual oil was stirred in 10 ml ether, cooled to −35° C. and then decanted. The residual oil was dried in the vacuum chamber of a glove box. Yield: 0.58 g, 92%. $^{31}P\{^1H\}$ NMR (CD$_3$CN, 122 MHz, δ ppm: −24.788 (s, 1 P) and −32.219 (s, 1P) (~95% pure). $^1$H NMR (CD$_3$CN, 300 MHz, δ: 7.533 to 7.361 (complex pattern, 5 H's on the Phenyl); 2.402(d of t, $J_{H-P}$=6.6 Hz and $J_{H-H}$=4.5 Hz, 8 H's on the —PCH$_2$—); 1.789 to 1.393 (complex, 12 H's on the two —CH$_2$CH$_2$CH$_2$— and 16 H's on PCH$_2$CH$_2$CH$_2$CN).

Example 22

Synthesis of ligand Q, PhP[(CH$_2$)$_3$P((CH$_2$)$_2$OC(O)CH$_3$)$_2$]$_2$

PhP[(CH$_2$)$_3$PH$_2$]$_2$ (0.460 g, 1.278 mmol), vinyl acetate (0.92 g, 10.7 mmol), AIBN (5 mg, 0.030 mmol) and toluene (1.5 g) were stirred and irradiated (365 nm) for about 16 hours in a vial with stirring. Some reddish brown solid formed on the bottom of the vial with clear liquid on top. The vial was then brought into a box and the solvent and excess vinyl acetate evaporated. Residual oil was stirred in 15 ml ether and filtered to remove the solid. The filtrate was evaporated to about 5 ml. Pentane (10 ml) was added and the vial was placed in the freezer at −35° C. The solvents were decanted and the oil pumped in the vacuum chamber to yield 0.73 g (68%) oil. $^{31}P\{^1H\}$ NMR (CDCl$_3$, 122 MHz, δ ppm: −25.801 (s, 1 P) and −39.029 (s, 2Ps) (~90% pure). $^1$H NMR (CDCl$_3$, 500 MHz, δ: 7.48 to 7.333 (complex pattern, 5 H's on the Phenyl); 4.150 (quintet, $J_{H-H,P}$=7.5 Hz, 8H's on the —PCH$_2$CH$_2$O—); 2.020(s, 12H's —COCH$_3$); 1.813 to 1.473 (complex, 12 H's on the two —CH$_2$CH$_2$CH$_2$— and 8 H's on PCH$_2$CH$_2$OC(O)CH$_3$).

Example 23

Synthesis of ligand R, PhP[(CH$_2$)$_3$P((CH$_2$)$_2$N(H)C(O)CH$_3$)$_2$]$_2$

PhP[(CH$_2$)$_3$PH$_2$]$_2$ (0.480 g, 1.86 mmol), vinyl acetamide (0.859 g, 10.0 mmol), AIBN (5 mg, 0.030 mmol) and toluene (1.5 g) were stirred and irradiated (365 nm) for about 16 hours in a vial with stirring. Solid formed on the bottom of the vial with clear liquid on top. The vial was then brought into a box and the clear liquid decanted. Residual oil was washed with 1.5 ml toluene. The solid was stirred in 15 ml THF. The solution was decanted and the solid dried in the vacuum chamber of the glove box to yield 0.722 g (66%) solid. $^{31}P\{^1H\}$ NMR (CD$_3$OD, 122 MHz, δ ppm: −25.246 and −25.369 (s and d?, 1 P) and −38.254 (s, 1.7P's) and −40.048 (d, $J_{P-P}$=8.2 Hz, 0.36P) (~99% pure assuming there are two isomers). $^1$H NMR (CD$_3$OD, 300 MHz, δ: 7.514 to 7.088 (complex pattern, 5 H's on the Phenyls of both isomers); 3.21 (complex, 8H's on the —PCH$_2$—); other peaks are not full assigned.

Example 24

Synthesis of ligand S, PhP[(CH$_2$)$_3$P-o-(CH$_2$C$_6$H$_4$CH$_2$)]$_2$

PhP[(CH$_2$)$_3$Cl]$_2$ (0.92 g, 3.5 mmol) and 2,3-dihydro-1H-isophosphindole (1.003 g, 7.2 mmol) were dissolved in 20 ml THF in a 100 ml Schlenk flask with a stir bar under nitrogen. The flask was cooled to −78° C. and LDA (4.5887 g 1.5 M solution, 8.44 mmol) was added dropwise. The reaction solution was allowed to warm up slowly overnight without removing the cold bath. The solvents were then removed under vacuum to obtain a white sticky paste. Toluene (30 ml) was added to dissolve the product. Water (20 ml) was added and the resulting mixture stirred for 10 minutes. The organic phase was then transferred into a flask containing MgOS$_4$ under nitrogen. The aqueous phase was extracted with toluene (2×10 ml) and the toluene extracts were combined. The toluene solution was then filtered in a glove box and the filtrated evaporated to obtain a white viscous oil. The oil was dissolve in 20 ml ether and filtered to remove small amount of solid. The filtrate was evaporated to about 2 ml. About 10 ml pentane was added to the ether solution and the resulting solution placed in the freezer at −35° C. An oil layer with a white solid crust was formed. The supernatant was decanted and the oil/solid was washed with 5 ml pentene and then dried under vacuum to obtain 0.927 g (57%). $^{31}P\{^1H\}$ NMR (CDCl$_3$, 122 MHz, δ ppm: −19.353 (s, 2Ps); −25.117 (s, 1P). $^1$H NMR (CDCl$_3$, 300 MHz, δ: 7.448 to 7.091 (complex pattern, 13 H's on the Phenyl and o-xylyls) and other peaks have not been fully assigned.

Example 25

Hydrogenation of Butyraldehyde Using Ligand D

In a glove box, a catalyst solution was prepared by adding a THF (10.00 g) solution of Rh(CO)$_2$acac (0.0321 g, 0.124 mmol) to a solution of Ligand D (0.0714 g, 0.163 mmol) in 12.00 g of THF and 5.00 g 1-propanol. A substrate solution was prepared by mixing butyraldehyde (4.00 g, which would result in an initial concentration of 1.50 M) and diglyme (1.00 g). An initial GC sample was taken from the butyraldebyde solution (0.10 ml) and diluted with THF. Under nitrogen, the catalyst solution was transferred into the reactor and the substrate solution was added into the substrate cylinder. Both solutions were purged three times with 300 psi 2:1 CO and hydrogpn gas. The reactor was then sealed, stirred and heated under 100 psi CO and 200 psi hydrogen. After the reaction solution was stirred for 15 minutes at 65° C., the pressure in the reactor was reduced to 200 psi and then the substrate solution was forced into the reactor with 300 psi 2:1 CO and hydrogen. The reactor was then fed with hydrogen from a 310 ml cylinder to maintain the reactor pressure at 300 psi. See Table 1 for detailed reaction conditions and reaction solution composition. Reaction times for every 7 psi hydrogen pressure drop in the 310 ml cylinder were recorded as shown in Table 2. A GC was taken when the reaction stopped consuming hydrogen gas, which took 20 minutes. This GC sample showed 99.2% conversion of butyraldehyde to 1-butanol. Butyraldehyde concentrations at various reaction times were calculated using the hydrogen gas consumption data and Ln[Butanal] was then plotted versus reaction time to generate a rate constant for this reaction (see FIG. 1). Using the reaction rate constant (−0.0053/second) and the initial concentration of buyraldehyde (C=1.494 M), the initial rate is calculated:

$$\text{Initial Rate} = -k \ast C = 0.053 \ast 1.494 \text{ M/second} = 0.00792 \text{ M/second} = 28.5 \text{ M/hour}.$$

TABLE 1

Conditions and catalyst solution composition for butanal hydrogenation using Ligand D

| Example | Ligand | Rh ppm | L/Rh | $P_{CO}$ | $P_{H2}$ | Delta P | Temp |
|---|---|---|---|---|---|---|---|
| 25 | D | 398 | 1.31 | 100 | 200 | 64 psi | 65° C. |

| Reagents | FW | d (g/ml) | wt. (g) | Vol (ml) | Mmol | Conc. M | wt % |
|---|---|---|---|---|---|---|---|
| Ligand D | 438.46 | 1.000 | 0.0714 | 0.07 | 0.163 | 0.004 | 0.222 |
| Rh(CO)$_2$acac | 258.04 | 1.000 | 0.0321 | 0.03 | 0.124 | 0.003 | 0.100 |
| THF | 72.11 | 0.889 | 22.00 | 24.75 | 305.089 | 8.199 | 68.404 |
| 1-Propanol | 60.10 | 0.804 | 5.0614 | 6.30 | 84.216 | 2.263 | 15.737 |
| Butanal | 72.11 | 0.800 | 4.0079 | 5.01 | 55.580 | 1.494 | 12.462 |
| Diglyme I.S. | 134.18 | 0.937 | 0.9889 | 1.06 | 7.370 | 0.198 | 3.075 |

Example 26

Hydrogenation of Butyraldehyde Using Ligand B through Ligand S

Similar procedures as described in Example 25 were employed to run the hydrogenation reactions using Ligand B through Ligand S. All reactions were run at 65° C. under 200 psi H$_2$ and 100 psi CO. Differences in reaction conditions, such solvents and rhodium concentrations, and results are shown in Table 3. Catalyst turnover per hour (TO/hour) rates are shown in Table 3 for easy comparison.

TABLE 3

Butyraldehyde hydrogenation rates (TO/hour) from reactions using the novel catalysts in 1-propanol (PrOH), THF and diglyme (internal GC standard) with an initial butyraldehyde concentration of 1.5 M. The prior art catalyst was also tested under similar conditions for comparison.

| Ligand | [Rh] ppm | [PrOH] wt % | [THF] wt % | Time 1 Min. | Conv. 1 Mol % | Rate[a] TO/hr. | Time 2 Min. | Conv. 2 Mol % |
|---|---|---|---|---|---|---|---|---|
| A | 401 | 16 | 68 | 5.00 | 42 | 2159 | 60 | 99 |
| B | 200 | 16 | 68 | 2.75 | 11 | 2218 | 68 | 87 |
| C | 301 | 16 | 68 | 15.00 | 21 | 505 | 269 | 99 |
| D | 398 | 16 | 68 | 0.75 | 26 | 9634 | 20 | 99 |
| E | 205 | 16 | 68 | 37.00 | 26 | 366 | 192 | 76 |
| F | 399 | 42 | 41 | 17.25 | 15 | 163 | 200 | 87 |
| G | 200 | 16 | 68 | 3.33 | 22 | 3548 | 57 | 99 |
| H | 403 | 27 | 46 | 3.78 | 20 | 1443 | 278 | 93 |
| I | 397 | 35 | 38 | 4.00 | 22 | 1577 | 86 | 95 |
| J | 405 | 35 | 38 | 40.00 | 16 | 109 | 40 | 16 |
| K | 400 | 16 | 68 | 3.60 | 20 | 1488 | 150 | 99 |
| L | 204 | 16 | 68 | 16.00 | 19 | 623 | 59 | 48 |
| M | 500 | 2.6[b] | 46 | 2.00 | 9.4 | 1149 | 42 | 99 |
| N | 500 | 2.6[b] | 46 | 9.93 | 34 | 837 | 50 | 98 |
| O | 411 | 16 | 68 | 17.8 | 20 | 302 | 230 | 89 |
| P | 405 | 16 | 68 | 0.92 | 21 | 5956 | 44 | 93 |
| Q | 401 | 16 | 68 | 5.50 | 27 | 1292 | 120 | 95 |
| R | 397 | 16 | 68 | 19.37 | 23 | 333 | 38 | 45 |

TABLE 3-continued

Butyraldehyde hydrogenation rates (TO/hour) from reactions using the novel catalysts in 1-propanol (PrOH), THF and diglyme (internal GC standard) with an initial butyraldehyde concentration of 1.5 M. The prior art catalyst was also tested under similar conditions for comparison.

| Ligand | [Rh] ppm | [PrOH] wt % | [THF] wt % | Time 1 Min. | Conv. 1 Mol % | Rate[a] TO/hr. | Time 2 Min. | Conv. 2 Mol % |
|---|---|---|---|---|---|---|---|---|
| S | 404 | 16 | 68 | 13.25 | 34 | 638 | 160 | 98 |
| PnBu$_3$ | 600 | 20 | 63 | 103 | 23 | 32 | 103 | 23 |

[a]Average catalyst turnover rates for the reaction time (Time 1) and the conversion (Conv. 1).
[b]These reactions also used 34 wt % hexane as co-solvent.

Example 27

Hydrogenation of Butyraldehyde Using Ligand G and L in the Presence of Water

The same procedures and reaction conditions as described in example 26 were employed to repeat the reactions using Ligand G and Ligand L, except that water (1.0 wt %) was added to the reaction solution. The results are shown in Table 4 in comparison to the reactions without water.

TABLE 4

Effect of water on catalysts promoted by Ligand G and Ligand L.

| Ligand | [Rh] ppm | H$_2$O wt % | Time Minutes | Conversion Mol % | Rate TO/hr. |
|---|---|---|---|---|---|
| G | 200 | 0.0 | 3.33 | 22 | 3548 |
|   | 202 | 1.0 | 4.00 | 19 | 2017 |
| L | 204 | 0.0 | 16.00 | 19 | 623 |
|   | 206 | 1.0 | 11.50 | 19 | 866 |

Example 28

Hydrogenation of Butyraldehyde Using Ligand B under Higher CO Pressures

Similar procedures as described in Example 25 were employed to run the hydrogenation reactions using Ligand B. Similar concentrations of rhodium (~200 ppm), ligand/Rh molar ratio (1.3/1), 1-propanol (~16 wt %) and butyraldehyde (1.5 M) were used for each reaction. The hydrogen pressure was 200 psi for all reactions and the CO pressures were 200 400 and 800 psi. The results are summarized in Table 5 in comparison to the reaction run with 100 psi of CO.

TABLE 5

Hydrogenation of butyraldehyde using Ligand B under higher CO pressures

| Reaction Number | [Rh] ppm | CO pressure psi | Time Minutes | Conversion Mol % | Rate TO/hr. |
|---|---|---|---|---|---|
| 1 | 201 | 100 | 2.75 | 11 | 2218 |
| 2 | 202 | 200 | 1.82 | 12 | 3346 |
| 3 | 205 | 400 | 1.50 | 10 | 3596 |
| 4 | 201 | 800 | 2.75 | 12 | 2444 |

Example 29

Hydrogenation of Butyraldehyde Using Ligand B with 2-propanol as a Co-Solvent

Similar procedures as described in Example 25 were employed to run the hydrogenation reactions using Ligand B. The reaction conditions and concentrations of rhodium (202 ppm), ligand/Rh molar ratio (1.3/1), and butyraldehyde (1.5 M) were the same as in reaction number 1 in Table 5, except that 2-propanol (16 wt %) was used in place of 1-propanol. A catalyst activation period was observed in this reaction. It took 6.53 minutes for the for first 12% conversion of butyraldehyde, which gave an average 1144 TO/hour. The next 10% conversion took only 2.32 minutes, which gave an average 2315 TO/hour.

Example 30

Hydrogenation of Butyraldehyde Using Ligand B with Methanol as a Co-Solvent

Similar procedures as described in Example 25 were employed to run the hydrogenation reactions using Ligand B. The initial reaction solution was comprised of rhodium (210 ppm), Ligand B (ligand/Rh molar ratio 1.3/1), butyraldehyde (1.5 M), THF (76.6 wt %), diglyme (2.3 wt % as GC internal standard) and methanol (8.3 wt %). Although the wt % concentration of methanol was lower than 1-propanol (16 wt %) in reaction number 1 in Table 6 hereinabove, the molar concentration (2.2 M) was the same as the molar concentration of 1-propanol in that reaction. The reaction was run at 65° C. with 100 psi CO and 215 psi hydrogen. The initial rate of hydrogenation was 2270 TO/hour for the for first 12% conversion of butyraldehyde.

Example 31

Reductive Hydroformylation of 1-Octene Using Mixed Catalysts of Ligand B and Ligand T

In a glove box, the following solutions were prepared: a hydrogenation catalyst solution containing Ligand B (0.1036 g, 0.2070 mmol) and Rh(CO)$_2$acac (0.0411 g, 0.1593 mmol) in THF (14.0 g) and 1-propanol (6.0 g); a hydroformylation catalyst solution containing hydroformylation ligand I (0.0864 g, 0.1007 mmol) and Rh(CO)$_2$acac (0.0206, 0.0798 mmol) in 13.0 g of THF; and a substrate solution containing 1-octene (5.500 g, 49.01 mmol) and diglyme (1.055 g, 11.57 mmol) as internal GC standard. An initial GC sample was taken from the substrate solution (0.10 ml) and diluted with THF. Under nitrogen, the hydrogenation catalyst solution was transferred into the reactor and the hydroformylation catalyst solution into a sample cylinder. The olefin solution was added into the substrate addition cylinder. The solutions in the reactor and the cylinders were purged three times with 300 psi 2:1 hydrogen and CO. The reactor was then sealed, stirred and heated under 300 psi 2:1 hydrogen and CO. After stirring the catalyst solution at target temperature for 15 minutes, the pressure in the reactor was reduced to 200 psi and then the hydroformylation catalyst solution was forced into the reactor under 300 psi 2:1 hydrogen and CO. After another 15 minutes, the pressure in the reactor was reduced to 240 psi and then the olefin solution was forced into the reactor with 300 psi 2:1 hydrogen and CO. The reactor was then fed with 300 psi 2:1 hydrogen and CO. Five GC samples were taken during the course of the reaction and the results are shown in Table 6.

TABLE 6

Results of reductive hydroformylation of 1-octene using Ligand B and Ligand T.

| Time | minutes | 10.00 | 30.00 | 60.00 | 90.00 | 120.00 |
|---|---|---|---|---|---|---|
| Octene consumption | Mol % | 44.6 | 79.3 | 91.7 | 96.6 | 99.5 |
| Aldehyde conversion | Mol % | 49.0 | 88.1 | 96.7 | 98.2 | 99.4 |
| Ave. rate of oxo reaction | Mol/L/hr | 2.11 | 1.30 | 0.79 | 0.55 | 0.43 |
| Ave. rate of hydrogenation | Mol/L/hr | 1.03 | 1.14 | 0.76 | 0.54 | 0.42 |
| N:I of aldehydes | Mol/mol | 40.2 | 15.6 | 7.5 | 6.3 | 3.7 |
| N:I of alcohols | Mol/mol |  | 139 | 96.9 | 81.2 | 73.9 |
| n-Nonanol selectivity | Mol % | 40.4 | 72.4 | 80.0 | 80.9 | 81.9 |

Example 32

Reductive Hydroformylation of 1-Octene and 1-butanal Using Mixed Catalysts of Ligand B and Ligand T In a glove box, the following solutions were prepared: a hydrogenation catalyst solution containing a MePh$_4$P$_3$Pr (0.0903 g, 0.1804 mmol) and Rh(CO)$_2$acac (0.0357 g, 0.1384 mmol) in THF (15.0 g) and 1-propanol (9.0 g); a hydroformylation catalyst solution containing Ligand T (0.250 g, 0.2976 mmol) and Rh(CO)$_2$acac (0.0359 g, 0.1391 mmol) in 10.0 g of THF; and a substrate solution containing 1-octene (4.500 g, 40.10 mmol), 1-butanal (4.20 g, 58.2 mmol) and diglyme (1.055 g, 11.5 mmol, as internal GC standard). An initial GC sample was taken from the substrate solution (0.10 ml) and diluted with THF. Under nitrogen, the hydrogenation catalyst solution was transferred into the reactor and the hydroformylation catalyst solution into a sample cylinder. The olefin solution was added into the substrate addition cylinder. The solutions in the reactor and the cylinders were purged three times with 300 psi 2:1 hydrogen and CO. The reactor was then sealed, stirred and heated under 300 psi 2:1 hydrogen and CO. After stirring at 65° C. for 15 minutes, the pressure in the reactor was reduced to 200 psi and then the hydroformylation catalyst solution was forced into the reactor under 300 psi 2:1 hydrogen and CO. After 30 minutes, the pressure in the reactor was reduced to 240 psi and then the olefin was forced into the reactor with 300 psi 2:1 hydrogen and CO. The reactor was then fed with 300 psi 2:1 hydrogen and CO with a slow purge to maintain 2:1 hydrogen and CO ratio in the reactor. Five GC samples were taken during the course of the reaction and the results are shown in Table 7.

TABLE 7

Results of reductive hydroformylation of 1-octene and 1-butanal using Ligand B and Ligand T.

| Time | Minutes | 6.25 | 16.00 | 32.75 | 174 | 1280 |
|---|---|---|---|---|---|---|
| Octene consumption | Mol % | 39.63 | 67.72 | 83.37 | 96.73 | 99.07 |
| Aldehyde conversion | Mol % | 21.83 | 43.30 | 61.93 | 92.29 | 98.85 |
| Ave. rate of oxo reaction | Mol/L/hr | 2.23 | 1.58 | 0.97 | 0.23 | 0.03 |
| Ave. rate of hydrogenation | Mol/L/hr | 2.75 | 2.46 | 1.88 | 0.58 | 0.08 |
| N:I of aldehydes | Mol/mol | 55.47 | 46.76 | 35.70 | 12.70 | #DIV/0! |
| N:I of alcohols | Mol/mol | #DIV/0! | 136.49 | 159.02 | 56.79 | 39.37 |
| n-Nonanol selectivity | Mol % | 12.6 | 29.3 | 46.9 | 78.1 | 86.9 |

Example 33

Hydrogenation of Butyraldehyde Using Ligand B in the Presence of 1-octene and Ligand T The procedures and reaction conditions in example 31 were employed to carry out the reaction using Ligand B, except that the ratio of Ligand B to Rh(CO)$_2$acac (total from both catalyst solutions) was 2:1 and the concentrations of both butanal and 1-octene was 1.0M. Detailed reaction solution composition is shown in Table 8 and the results are shown in Table 9.

TABLE 8

Reaction solution composition for example 33.

| Reagents | FW | d (g/ml) | wt. (g) | vol (ml) | mmol | M | w % |
|---|---|---|---|---|---|---|---|
| Ligand B | 500.54 | 1.000 | 0.1950 | 0.1950 | 0.3896 | 0.0069 | 0.0001 |
| Ligand T | 840.00 | 1.000 | 0.1218 | 0.1218 | 150.55 | 2.6807 | 0.0569 |
| Rh(CO)2acac | 258.04 | 1.000 | 0.0478 | 0.0478 | 0.1852 | 0.0033 | 0.0001 |
| THF | 72.11 | 0.889 | 25.0000 | 28.1215 | 346.69 | 6.1734 | 0.1310 |
| 1-Propanol | 60.10 | 0.804 | 9.0479 | 11.2536 | 150.55 | 2.6807 | 0.0569 |
| Butanal | 72.11 | 0.800 | 4.2000 | 5.2500 | 58.24 | 1.0371 | 0.0220 |
| Diglyme | 134.18 | 0.937 | 2.0011 | 2.1356 | 14.91 | 0.2656 | 0.0056 |
| 1-Octenes | 112.22 | 0.720 | 6.5042 | 9.0336 | 57.96 | 1.0321 | 0.0219 |

TABLE 9

Reaction results from example 33.

| Reaction time | Minutes | 6.67 | 52.50 |
|---|---|---|---|
| Octene consumption | Mol % | 0.00 | 0.00 |
| Butanal conversion | Mol % | 59.11 | 96.81 |
| Average rate of hydroformylation | Mol/L/hour | 0.00 | 0.00 |
| Average rate of hydrogenation for the conversion | Mol/L/hour | 5.41 | 1.16 |

Example 34

Reductive Hydroformylation of 1-Octene Using Mixed Catalysts of Ligand B and Ligand U The procedures in example 31 were employed to carry out the reaction using Ligand B and Ligand U. This example was the second addition of 1-octene into the reactor so that there was already n-nonanal and 2-methyl-1-octanal in the reactor. The reaction was carried out under 90 psi CO, 180 psi hydrogen at 55° C. The catalyst solution composition is shown in Table 10 and the results in Table 11.

TABLE 10

Conditions and catalyst solution composition for mixed catalysts of Ligand B and Ligand U.

| Reagents | FW | d (g/ml) | wt. (g) | vol (ml) | Mmol | M | w % |
|---|---|---|---|---|---|---|---|
| Ligand B | 500.54 | 1 | 0.0570 | 0.06 | 0.1138 | 0.0024 | 0.14 |
| Ligand U | 1095.62 | 1 | 0.1553 | 0.16 | 0.1417 | 0.0030 | 0.37 |
| Rh(CO)$_2$acac | 258.04 | 1 | 0.0459 | 0.05 | 0.1747 | 0.0038 | 0.11 |
| Tetraglyme | 222 | 1.009 | 18.0428 | 17.88 | 81.27 | 1.7059 | 43.35 |
| 1-Propanol | 60.1 | 0.804 | 11.7104 | 14.57 | 194.85 | 4.0897 | 28.13 |
| Diglyme I.S. | 134.18 | 0.94 | 0.9882 | 1.05 | 7.37 | 0.1548 | 2.37 |
| C9 alcohols | 144.24 | 0.80 | 2.1460 | 2.68 | 14.88 | 0.3123 | 5.16 |
| C9 aldehydes | 142.24 | 0.80 | 4.0650 | 5.08 | 28.58 | 0.5998 | 9.77 |
| 1-Octenes | 112.22 | 0.72 | 4.2320 | 5.88 | 37.71 | 0.7915 | 10.17 |
| Diisopropylethylamine | 129 | 0.74 | 0.1800 | 0.24 | 1.40 | 0.0293 | 0.43 |

TABLE 11

Results of reductive hydroformylation of 1-octene using catalysts of Ligand B and Ligand U.

| Reaction Time | minutes | 10 | 25 | 55 | 85 | 140 |
|---|---|---|---|---|---|---|
| 1-Octene consumption | Mol % | 31 | 67 | 92 | 97 | 99 |
| Aldehyde conversion | Mol % | 43 | 43 | 68 | 91 | 99 |
| Ave. rate of oxo reaction | Mol/L/hr | 1.5 | 1.3 | .79 | .53 | .33 |
| Ave. rate of hydrogenation | Mol/L/hr | .62 | .54 | .53 | .48 | .33 |
| N:I of aldehydes | Mol/mol | 21 | 20 | 15 | 5 | |
| N:I of alcohols | Mol/mol | 60 | 62 | 52 | 52 | 38 |
| n-Nonanol selectivity | Mol % | 39 | 38 | 61 | 81 | 90 |

What is claimed is:

1. A process for hydrogenation of aldehydes to alcohols comprising the steps of:
    a. providing an aldehyde selected from the group consisting of 2 to 60 carbon atoms;
    b. providing a homogeneous catalyst produced by mixing a rhodium catalyst precursor and a ligand of formula I

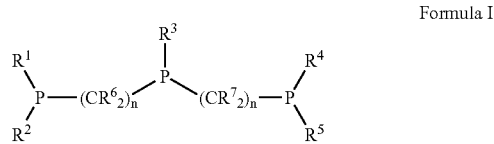

Formula I wherein n is 3 to 5, R1, R2, R3, R4 and R5 are hydrocarbyl radicals and each $R^6$ and $R^7$ is individually selected from the group consisting of alkyl, aryl, and hydrogen radicals;
    c. hydrogenating the aldehyde in any suitable solvent that does not interfere with the hydrogenation catalyst to form an alcohol.

2. The hydrogenation process of claim 1 in a solvent selected from the group consisting of ethers, alcohols, aromatics, alkanes and mixtures thereof at a concentration of from about 0.1 Mol/L to about 10 Mol/L %, with the exception that the alcohol solvent is less than about 8 Mol/L.

3. The hydrogenation process of claim 2 wherein the ether is selected from the group consisting of diethyl ether, tetrahydrofuran, diglyme and tetraglyme.

4. The hydrogenation process of claim 2 wherein the alcohol selected from the group consisting of methanol, ethanol, 1-propanol, 2-propanol, butanol, pentanol, hexanol, heptanol, octanol and nonanol.

5. The hydrogenation process of claim 2 wherein the aromatic is toluene.

6. The hydrogenation process of claim 2 wherein the alkane is hexane.

7. The hydrogenation process of claim 1 wherein the aldehyde is generated in situ by reacting an olefin with a hydroformylation catalyst promoted by a bis-chelating phosphorus ligand.

8. The hydrogenation process of claim 7 wherein the bis-chelating phosphorus ligand is selected from the group consisting of ligands T and U:

Ligand T
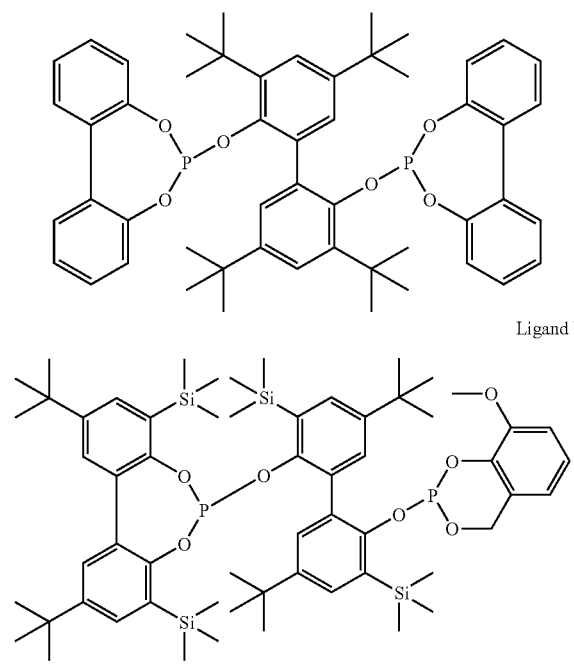
Ligand U
9. The process of claim 1 wherein the ligand of Formula I is selected from the group consisting of:
Ligand A
Ligand B
Ligand C
Ligand D
Ligand E
Ligand F
Ligand G
Ligand H
Ligand I
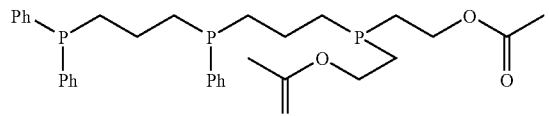
Ligand J
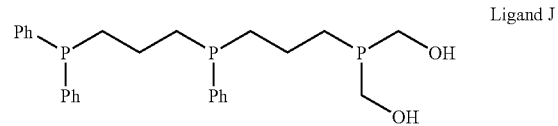
Ligand K
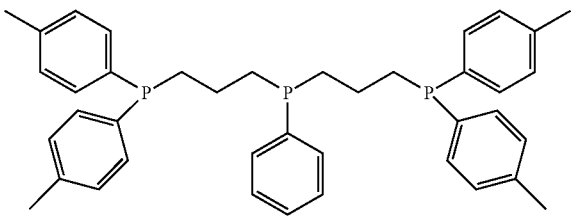
Ligand L
Ligand M
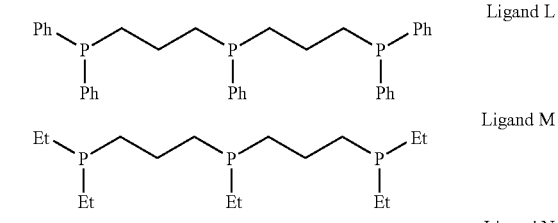
Ligand N
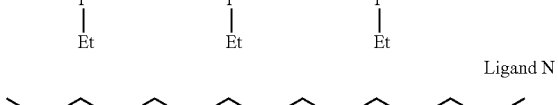
Ligand O
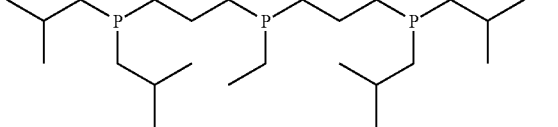
Ligand P
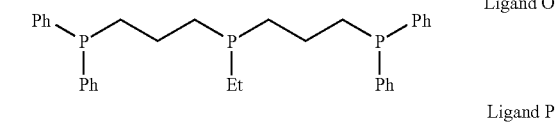
Ligand Q
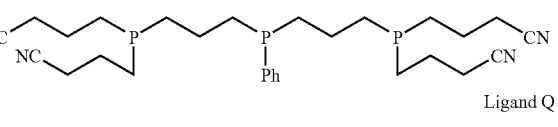
Ligand R
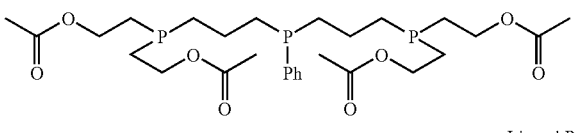
and
Ligand S
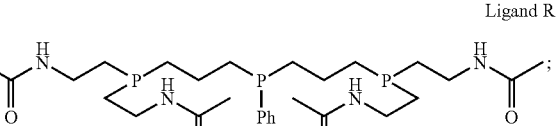
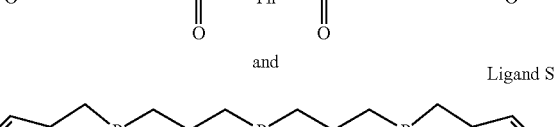
* * * * *